(12) United States Patent
Nakashima

(10) Patent No.: US 6,533,722 B2
(45) Date of Patent: Mar. 18, 2003

(54) ELECTRONIC ENDOSCOPE HAVING REDUCED DIAMETER

(75) Inventor: Masaaki Nakashima, Tokyo (JP)

(73) Assignee: Pentax Corporation, Tokyo (JP)

( * ) Notice: Subject to any disclaimer, the term of this patent is extended or adjusted under 35 U.S.C. 154(b) by 123 days.

(21) Appl. No.: 09/726,342

(22) Filed: Dec. 1, 2000

(65) Prior Publication Data

US 2001/0007051 A1 Jul. 5, 2001

(30) Foreign Application Priority Data

Dec. 3, 1999 (JP) ............................................ 11-344987

(51) Int. Cl.[7] ................................................ A61B 1/07
(52) U.S. Cl. ........................ 600/179; 600/129; 600/130
(58) Field of Search ................................. 600/109, 179, 600/178, 129, 130, 182, 160; 348/68, 76; 433/29, 30

(56) References Cited

U.S. PATENT DOCUMENTS

| | | | | |
|---|---|---|---|---|
| 4,691,253 A | * | 9/1987 | Silver | ............................ 358/906 |
| 5,343,244 A | * | 8/1994 | Sase et al. | ................. 348/222.1 |
| 5,523,782 A | * | 6/1996 | Williams | ...................... 348/66 |
| 3,279,460 A | * | 10/1996 | Sheldon | ......................... 600/129 |
| 5,604,531 A | * | 2/1997 | Iddan et al. | ................... 348/76 |
| 5,644,438 A | * | 7/1997 | Pottash | ......................... 359/367 |
| 5,745,165 A | * | 4/1998 | Atsuta et al. | .................. 348/65 |
| 5,908,294 A | * | 6/1999 | Schick et al. | ................. 433/29 |
| 6,095,970 A | | 8/2000 | Hidaka et al. | |

FOREIGN PATENT DOCUMENTS

| | | | |
|---|---|---|---|
| DE | 29613103 | * | 11/1997 |
| JP | 8-117184 | * | 5/1996 |

* cited by examiner

Primary Examiner—John P. Leubecker
(74) Attorney, Agent, or Firm—Greenblum & Bernstein, P.L.C.

(57) ABSTRACT

An electronic endoscope has a tip portion with a tip end. This electronic endoscope comprises an imaging element provided in the tip portion; an imaging optical system provided in the tip portion at a position closer to the tip end than the imaging element; and a plurality of light-emitting elements for emitting light, each of which is provided in the tip portion at a position closer to the tip end than the imaging element. Each of the light-emitting elements is arranged such that a part of the light-emitting element is seen so as to overlap with the imaging element when viewed from the optical axis direction of the imaging optical system. According to this arrangement, it is possible to reduce the diameter of the tip portion of the electronic endoscope. Further, when such an electronic endoscope is used as a medical endoscope, it becomes possible to relieve the pain that patients may feel.

26 Claims, 11 Drawing Sheets

Horizontal Scanning Direction

Horizontal Scanning Direction →

Horizontal Scanning Direction →

ELECTRONIC ENDOSCOPE HAVING REDUCED DIAMETER

BACKGROUND OF THE INVENTION

1. Field of the Invention

The present invention relates to an electronic endoscope.

2. Description of the Prior Art

In the medical field, for example, electronic endoscope systems have been used as diagnostic systems for examining internal portions (e.g., the alimentary canal) of the human body.

In general, such electronic endoscope systems include a light source device and an electronic endoscope which is removably mounted (connected) to the light source device.

FIG. 11 is a bottom view and a cross-sectional view of a tip portion of the prior-art electronic endoscope.

As shown in FIG. 11, the prior-art electronic endoscope 100 includes an endoscope main body 110. In a tip portion 120 of the endoscope main body 110, there are provided a CCD imaging sensor (imaging element) 130 and a pair of light-emitting diodes (light-emitting elements) 140 for emitting light toward an observation part of a patient.

In this prior-art electronic endoscope 100, these light-emitting diodes 140 are arranged at the opposite sides of the CCD imaging sensor 130 as shown in FIG. 11.

Further, in front of the CCD imaging sensor 130, there is provided an imaging optical system that includes an objective lens 150 and convex lenses 160 and 170.

Furthermore, a diverging lens (light distribution lens) 180 is provided in front of each of the light-emitting diodes 140.

However, in the prior-art electronic endoscope 100 the light-emitting diodes 140 are arranged at the opposite sides of the CCD imaging sensor 130, and this results in a problem that the diameter of the endoscope main body 110 of the electronic endoscope 100 becomes large.

SUMMARY OF THE INVENTION

Therefore, it is an object of the present invention to provide an electronic endoscope provided with an endoscope main body that has a relatively small diameter.

In view of the object, the present invention is directed to an electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion at a position closer to the tip end than the imaging element; and a light-emitting element for emitting light toward an observation part of the object, the light-emitting element being provided in the tip portion at a position closer to the tip end than the imaging element, wherein the light-emitting element is arranged such that at least a part of the light-emitting element is seen so as to overlap with the imaging element when viewed from the optical axis direction of the imaging optical system.

According to the present invention described above, the light-emitting element is provided in the tip portion at a position closer to the tip end then the imaging element. In addition, the light-emitting element is arranged such that at least a part of the light-emitting element is seen so as to overlap with the imaging element when viewed from the optical axis direction of the imaging optical system. As a result of this arrangement, it becomes possible to reduce the diameter of the electronic endoscope, in particular, the diameter of the tip portion of the electronic endoscope. Further, when such an electronic endoscope that has a small diameter is used as a medical endoscope, it becomes possible to relieve the pain that patients may feel during diagnosis.

In this invention, it is preferred that the imaging element has an imaging region that includes at least one shading region for detecting a reference level of optical black, in which the light-emitting element is arranged so that at least a part of the light-emitting element is seen so as to overlap with the shading region of the imaging element when viewed from the optical axis direction of the imaging optical system.

Further, in this invention, it is also preferred that the imaging optical system includes a light-deflecting member for deflecting light rays from the observation part of the object. In this case, it is preferred that the imaging element has an imaging region that includes at least one shading region for detecting a reference level of optical black, in which the light-emitting element is arranged such that at least a part of the light-emitting element is situated within the region of light rays being directed to the shading region of the imaging element.

Furthermore, in this invention, it is also preferred that the imaging element has an imaging region that includes an effective imaging region on which an image is to be formed by light rays that have passed through the imaging optical system.

Moreover, in this invention, it is also preferred that the light-emitting element includes a light-emitting diode.

Another aspect of the present invention is directed to an electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion in front of the imaging element along the optical axis; and a light-emitting element for emitting light toward an observation part of the object, the light-emitting element being provided in the tip portion at a position closer to the tip end than the imaging element, wherein the light-emitting element is arranged such that at least a part of a projected image which could be formed by projecting the light-emitting element onto a projecting surface perpendicular to the optical axis of the imaging optical system overlaps with a projected image which could be formed by projecting the imaging element onto the projecting surface perpendicular to the optical axis.

In this invention, it is preferred that the imaging element has an imaging region that includes at least one shading region for detecting a reference level of optical block, in which the light-emitting element is arranged such that at least a part of a projected image which could be formed by projecting the light-emitting element onto the projecting surface perpendicular to the optical axis overlaps with a projected image which could be formed by projecting the imaging region of the imaging element onto the projecting surface perpendicular to the optical axis.

Further, in this invention, it is also preferred that the electronic endoscope further comprises a light-deflecting member for deflecting light rays emitted from the light-emitting element, wherein the light-deflecting member is provided in front of the light-emitting element.

Further, in this invention, it is also preferred that the imaging optical system includes a light-deflecting member for deflecting light rays from the observation part of the object.

Moreover, in this invention, it is also preferred that the imaging element has an imaging region that includes an effective imaging region on which an image is to be formed by light rays that have passed through the imaging optical system.

Still further, in this invention, it is also preferred that the light-emitting element includes a light-emitting diode.

Yet another aspect of the present invention is directed to an electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion at a position closer to the tip end than the imaging element; and a plurality of light-emitting elements for emitting light toward an observation part of the object, each of the light-emitting elements being provided in the tip portion at a position closer to the tip end than the imaging element, wherein each of the light-emitting elements is arranged such that at least a part of the light-emitting element is seen so as to overlap with the imaging element when viewed from the optical axis direction of the imaging optical system Yet another aspect of the present invention is directed to an electronic endoscope having a tip portion which is to be inserted into an object to be observed, the electronic endoscope comprising:

an imaging element provided in the tip portion;

an imaging optical system having an optical axis, the imaging optical system being provided in the tip portion in front of the imaging element along the optical axis; and a plurality of light-emitting elements for emitting light toward an observation part of the object, each of the light-emitting elements being provided in the tip portion at a position closer to the tip end than the imaging element, wherein each of the light-emitting elements is arranged such that at least a part of a projected image which could be formed by projecting the light-emitting element onto a projecting surface perpendicular to the optical axis of the imaging optical system overlaps with a projected image which could be formed by projecting the imaging element onto the projecting surface perpendicular to the optical axis.

These and other objects, structures and advantages of the present invention will be apparent more clearly when the following detailed description of the preferred embodiments is considered taken in conjunction with the accompanying drawings.

DETAILED DESCRIPTION OF THE PREFERRED EMBODIMENTS

A detailed description of the preferred embodiments of an electronic endoscope according to the present invention will now be given below with reference to the appended drawings.

Figure 1:
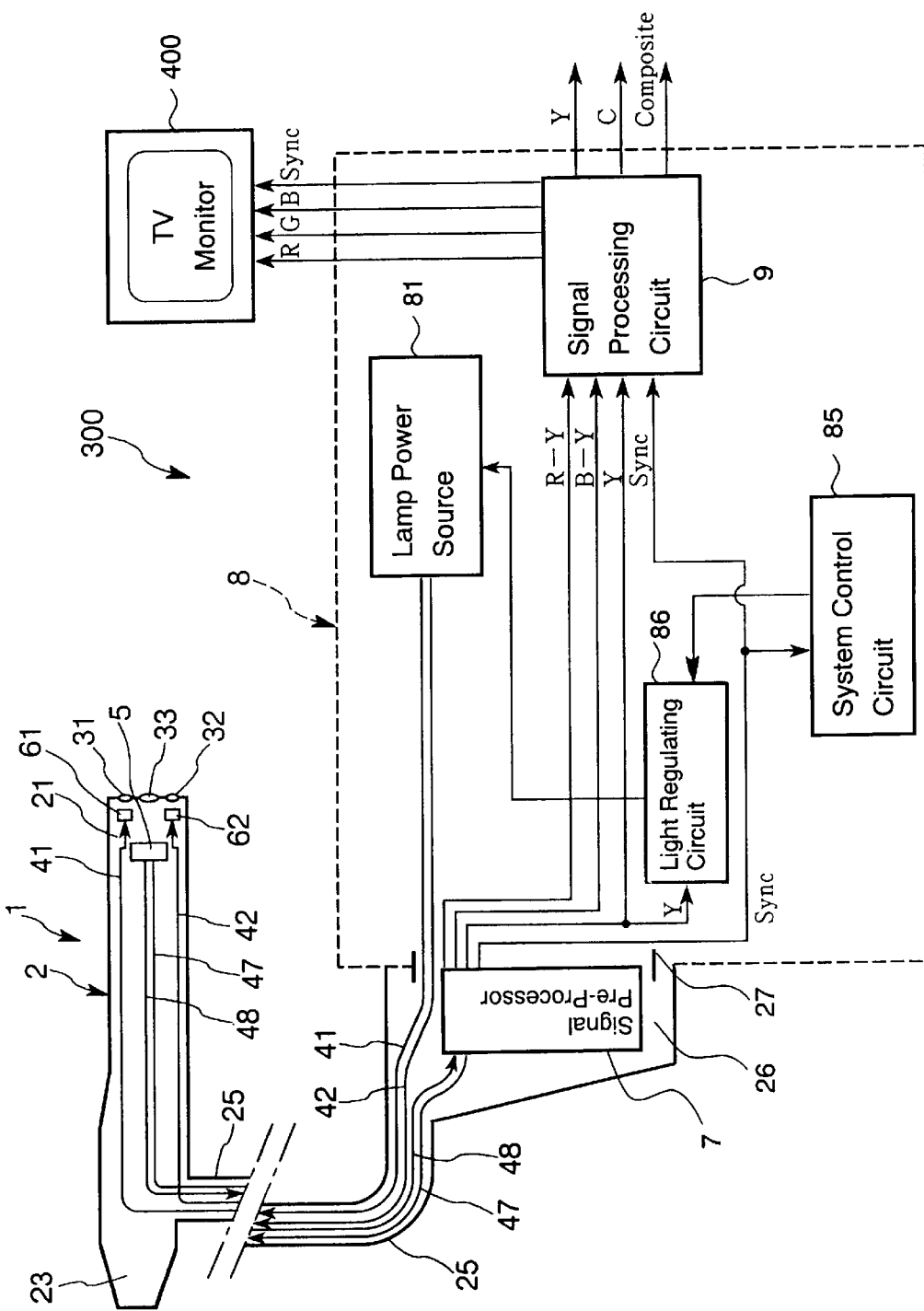
FIG. 1 is a block diagram which shows a first embodiment of an electronic endoscope according to the present invention and the structure of a light source device to which the electronic endoscope is connected.
Figure 2:
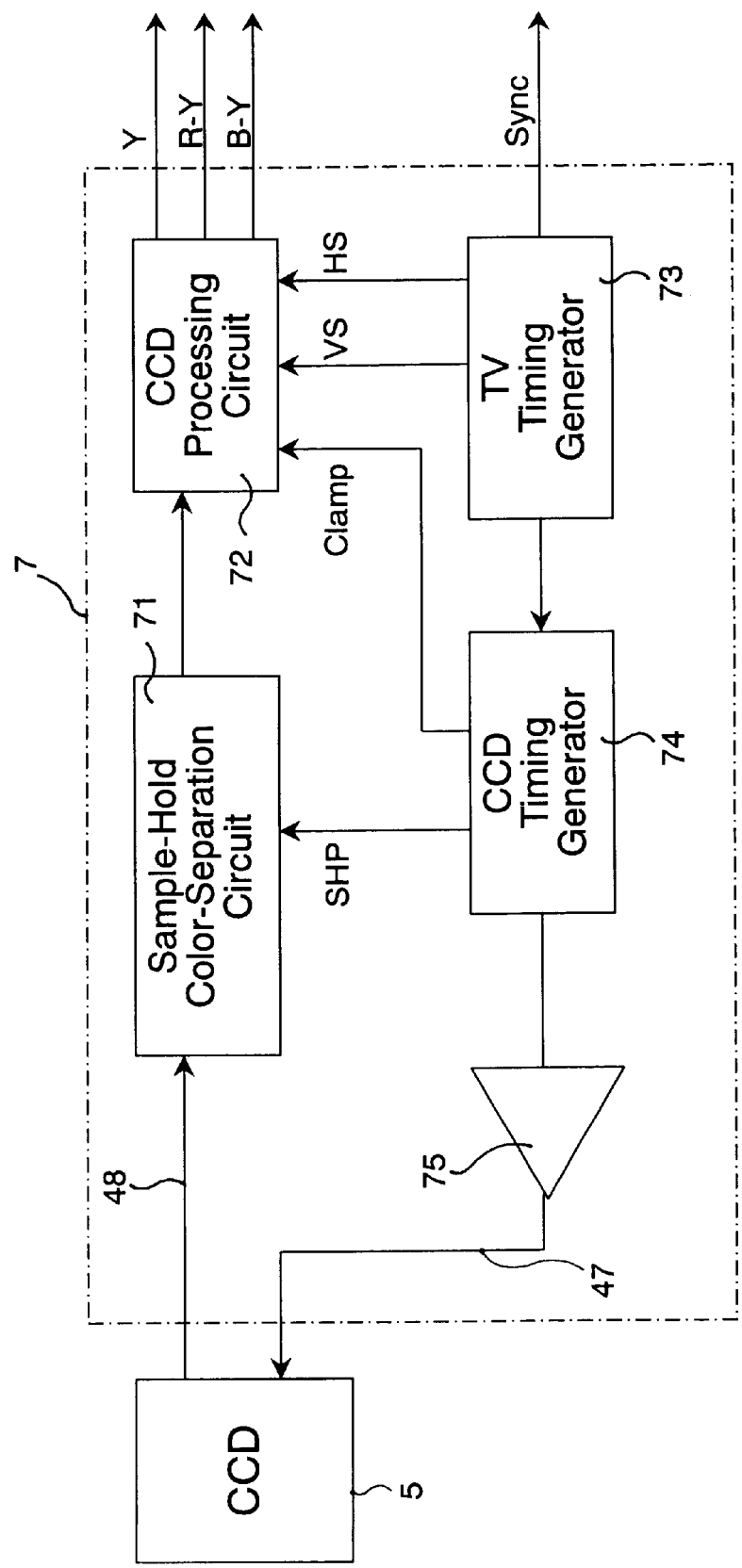
FIG. 2 is a block diagram which shows the structure of a signal pre-processor of the electronic endoscope shown in FIG. 1.
Figure 3:
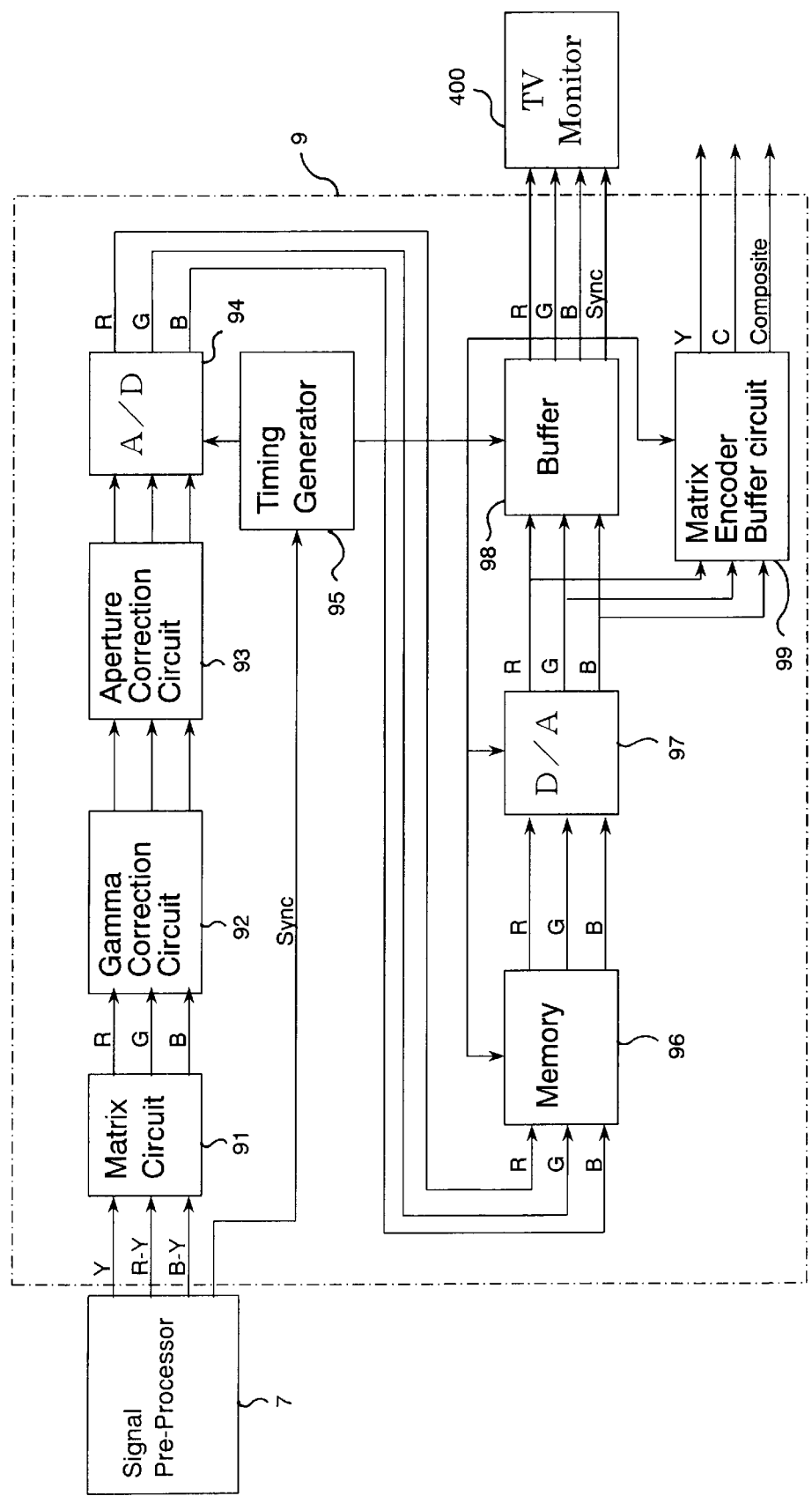
FIG. 3 is a block diagram which shows the structure of a signal processing circuit of the light source device shown in FIG. 1.
Figure 4:
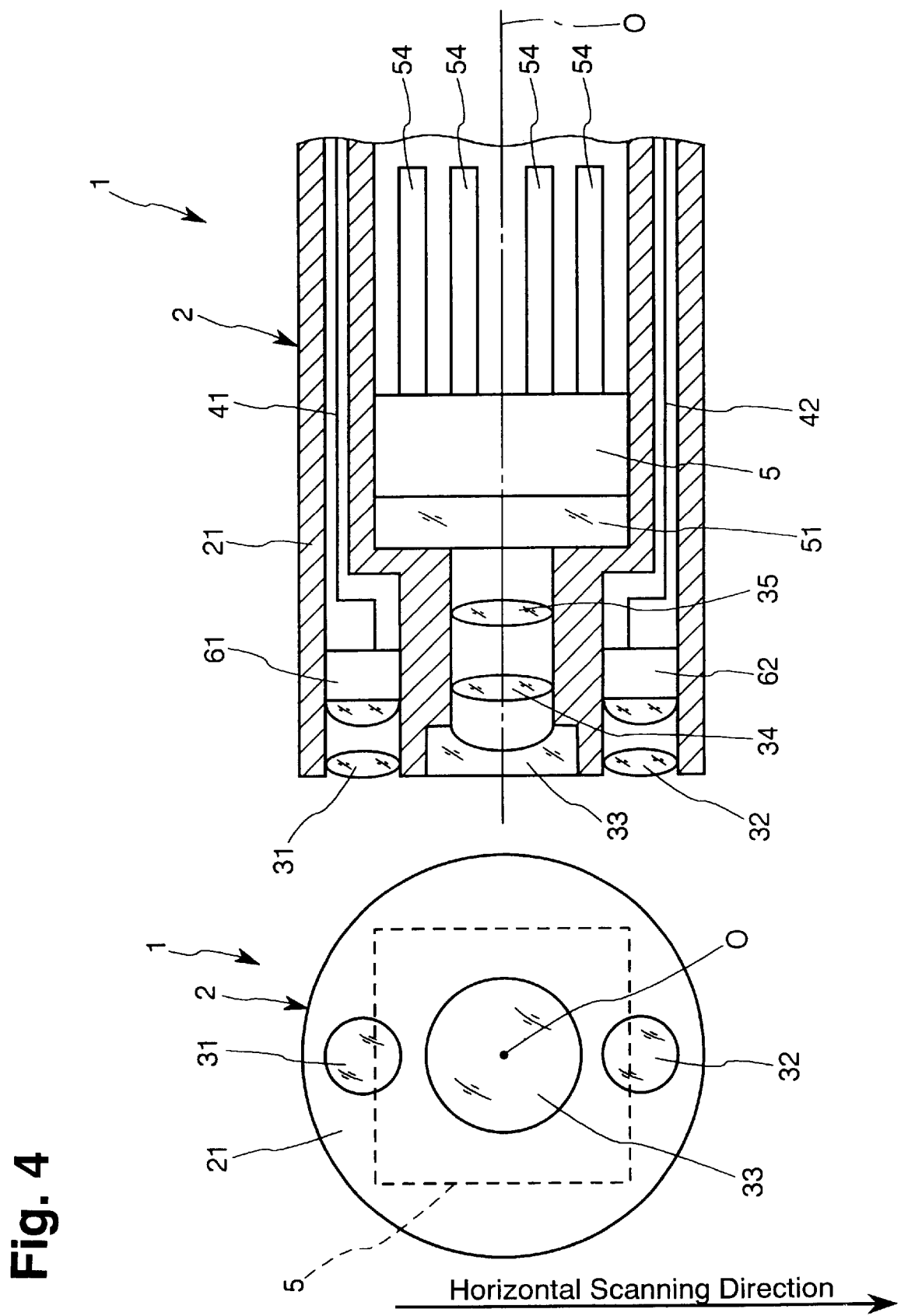
FIG. 4 is a bottom view and a cross-sectional view of the tip portion of the electronic endoscope shown in FIG. 1.
Figure 5:
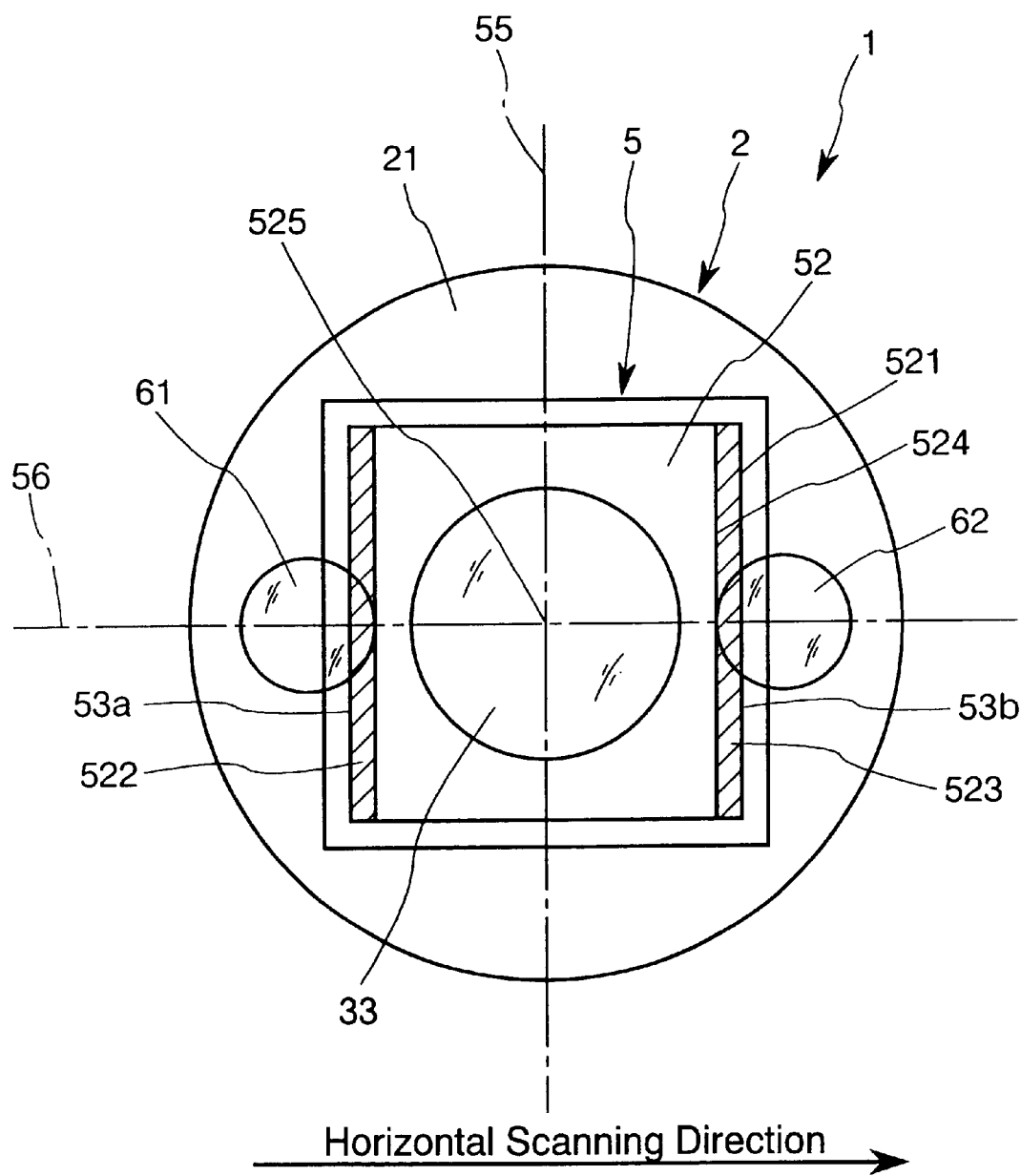
FIG. 5 is a bottom view of the tip portion of the electronic endoscope shown in FIG. 1, in which an endoscope main body, a CCD imaging sensor, an objective lens and light-emitting diodes are shown as being viewed from the optical axis direction of an imaging optical system.

FIG. 1 is a block diagram which shows a first embodiment of an electronic endoscope according to the present invention and the structure of a light source device to which the electronic endoscope is connected. FIG. 2 is a block diagram which shows the structure of a signal pre-processor of the electronic endoscope shown in FIG. 1. FIG. 3 is a block diagram which shows the structure of a signal processing circuit of the light source device shown in FIG. 1. FIG. 4 is a bottom view and a cross-sectional view of the tip portion of the electronic endoscope shown in FIG. 1. FIG. 5 is a bottom view of the tip portion of the electronic endoscope shown in FIG. 1, in which an endoscope main body, a CCD imaging sensor, an objective lens and light-emitting diodes are shown as being viewed from the optical axis direction of an imaging optical system.

Hereinafter, for easier understanding, the right and left directions in the cross-sectional view of FIG. 4 will be simply referred to as an "optical axis direction" of the imaging optical system. Further, the left side in this figure will be referred to as "tip", and the right side will be referred to as "base". Furthermore, an end at the side of the tip of the tip portion of the main body will be referred as a "tip end."

As shown in FIG. 1, an electronic endoscope system (endoscope system) 300 includes a light source device 8 and an electronic endoscope 1 which is removably connected to the light source device 8. (Hereinafter, the electronic endoscope will be simply referred to as an "endoscope.")

The endoscope 1 is equipped with a long flexible (elastic) endoscope main body 2. (Hereinafter, the endoscope main body is simply referred to as a "main body.") The main body 2 includes an operation portion 23 provided at the base end portion thereof.

As shown in FIG. 4, in the central portion of the tip portion 21 of the main body 2, there are provided an imaging optical system including an objective lens 33 and convex lenses 34 and 35; and a CCD (Charge Coupled Device) imaging sensor (imaging element) 5 that includes a transparent glass cover 51 having light transmittivity. The objective lens 33, the convex lenses 34 and 35 and the CCD imaging sensor 5 are arranged in this order from the tip (i.e., the left side in FIG. 4) to the base (i.e., the right side in FIG. 4). In this structure, the imaging optical system is arranged in front of the CCD imaging sensor 5 along the optical axis O. In other words, the imaging optical system is provided in the tip portion 21 at a position closer to the tip end of the tip portion 21 than the CCD imaging sensor 5.

The objective lens 33 is formed from a concave lens, and has the largest diameter among the lenses in the imaging optical system.

As shown in FIGS. 4 and 5, the CCD imaging sensor 5 (from which lead wires 54 are excluded) has a roughly rectangular parallelepiped shape.

Further, as shown in FIG. 5, an imaging region 521 of the CCD imaging sensor 5 has a rectangular shape.

On each of the opposite short sides 53a and 53b (i.e., the sides positioned at both ends along the horizontal scanning direction in FIG. 5) of the imaging region 521 of the CCD imaging sensor 5, band-shaped shading regions 522 and 523 (shown by the slanting lines in FIG. 5) for detecting a reference level of optical black are provided, respectively. Each of the shading regions 522 and 523 is normally referred to as "optical black (optical black portion)." In this connection, the imaging region 521 from which the shading regions 522 and 523 are excluded functions as an effective imaging region 524.

In this embodiment, the shading region 522 has a width that is constant in the direction of a line parallel to the short side 53a, and the shading region 523 has a width that is constant in the direction of a line parallel to the short side 53b. Further, the width of the shading region 522 and the width of the shading region 523 are set to be equal to each other.

Further, as shown in FIGS. 4 and 5, the CCD imaging sensor 5 is arranged such that the optical axis O of the imaging optical system passes through the center 525 of the effective imaging region 524 of the CCD imaging sensor 5, and that the shading regions 522 and 523 of the imaging region 521 are symmetrically positioned with respect to the optical axis O.

Furthermore, as shown in FIG. 4, in the tip portion 21 of the main body 2, there are provided a pair of diverging lenses (light distribution lenses) 31 and 32, and a pair of light-emitting diodes (light-emitting elements) 61 and 62. The diverging lenses 31 and 32 are respectively arranged in front of the corresponding light-emitting diodes 61 and 62. Namely, each of the diverging lenses 31 and 32 is arranged at the tip side of the corresponding light-emitting diode.

Each of the diverging lenses 31 and 32 is formed from a convex lens, and has substantially the same diameter as that of the corresponding light-emitting diode. Specifically, each of the light-emitting diodes 61 and 62 is arranged so that its center is substantially aligned with the center of the corresponding diverging lens when viewed from the optical axis direction of the imaging optical system. (Hereinafter, the optical axis direction of the imaging optical system is simply referred to as the "optical axis direction.")

In this connection, as for the light-emitting element of the present invention, a lamp which generates (emits) light by supplying electrical power thereto may be used if it has such shape and size that can be housed within the tip portion of the endoscope. However, a light-emitting diode should preferably be used in this invention, since such a light-emitting diode has a small size and it can be used for a long period of time with a small amount of electrical power.

Next, the arrangement of each of light-emitting diodes 61 and 62 will be described in more detail.

As shown in FIG. 4, each of the light-emitting diodes 61 and 62 is provided in front of the CCD imaging sensor 5 along the optical axis O. In other words, each of the light-emitting diodes 61 and 62 is provided in the tip portion 21 at a position closer to the tip end of the tip portion 21 than the CCD imaging sensor 5. Further, these light-emitting diodes 61 and 62 are respectively arranged at opposite sides of the CCD imaging sensor 5 so that the imaging optical system (which includes the objective lens 33 and convex lenses 34 and 35) is positioned between the light-emitting diodes 61 and 62 when viewed from the optical axis direction.

Specifically, as shown in FIG. 5, each of the light-emitting diodes 61 and 62 is arranged such that a part of each light emitting diode 61 (62) is seen so as to overlap with the CCD imaging sensor 5 when viewed from the optical axis direction, but not to overlap with the imaging optical system (which includes the objective lens 33 and convex lenses 34 and 35) and the effective imaging region 524 of the CCD imaging sensor 5.

In other words, in the endoscope of this invention, each of the light-emitting diodes 61 and 62 is arranged outside light rays that form an image on the effective imaging region 524 of the CCD imaging sensor 5 through the imaging optical system. Further, each of the light-emitting diodes 61 and 62 is arranged such that a part of each of the light-emitting diodes 61 and 62 is seen so as to overlap with the CCD imaging sensor 5 when viewed from the optical axis direction.

In more details, in this embodiment, the light-emitting diodes 61 and 62 are arranged such that a part of the light-emitting diode 61 is seen so as to overlap with the shading region 522 when viewed from the optical axis direction, and such that a part of the light-emitting diode 62 is seen so as to overlap with the shading region 523 when viewed from the optical axis direction.

Further, in this embodiment, the light-emitting diodes 61 and 62 are symmetrically positioned with respect to a first center line (straight line) 55 that is orthogonal to the horizontal scanning direction in the CCD imaging sensor 5 and that passes through the center 525 of the effective imaging region 524 of the CCD imaging sensor 5. In addition, the light-emitting diodes 61 and 62 are also symmetrically positioned with respect to a second center line (straight line) 56 that is in parallel with the horizontal scanning direction in the CCD imaging sensor 5 and that passes through the center 525 of the effective imaging region 524 of the CCD imaging sensor 5.

According to the present invention described above, the endoscope is provided with even number of light-emitting diodes (two light-emitting diodes in this embodiment), and the light-emitting diodes are symmetrically positioned with respect to each of the first and second center lines 55 and 56. By constructing the endoscope in this way, it becomes possible to illuminate an observation part of an object (e.g., a patient) more uniformly.

As shown in FIG. 1, one end of a universal cord (cord-shaped coupling) 25 is connected to the base end portion of the main body 2.

The other end of the universal cord 25 is provided with a connecting portion 26 equipped with a connector 27. By means of the connector 27, the endoscope 1 is removably connected to the light source device 8 to establish an electrical connection therebetween.

Further, a signal pre-processor 7 which is electrically connected to the connector 27 is housed inside the connecting portion 26, and the CCD imaging sensor 5 is electrically connected to the signal pre-processor 7 via signal lines 47 and 48.

Furthermore, the light-emitting diodes 61 and 62 are electrically connected to the connector 27 via the lead wires 41 and 42, respectively.

As shown in FIG. 2, the signal pre-processor 7 of the endoscope 1 includes a sample-hold and color-separation circuit 71, a CCD processing circuit (clamping circuit) 72, a television timing generator 73, a CCD timing generator 74 and a buffer 75.

As shown in FIG. 1, the light source device 8 includes a lamp power source 81, a system control circuit (control means) 85, a light regulating circuit 86 and a signal processing circuit 9 which are all housed in a casing not shown in the drawings.

As shown in FIG. 3, the signal processing circuit 9 of the light source device 8 includes a matrix circuit 91, a gamma correction circuit 92, an aperture correction circuit 93, an A/D converter 94, a timing generator 95, a memory 96, a D/A converter 97, a buffer 98 and a matrix encoder buffer circuit 99.

Further, a television monitor (display means) 400 for displaying images at an observation part (e.g., affected part of a patient) is removably connected to the light source device 8.

Next, the operation of the electronic endoscope system 300 will be described with reference to FIGS. 1 to 3.

As shown in FIG. 1, when the power supply is turned on, electrical power is supplied from the lamp power source 81 to the light-emitting diodes 61 and 62, and this causes each light-emitting diode to emit light. The level of voltage generated in the lamp power source 81 is controlled between a high level and a low level (i.e., zero volt) by the system control circuit 85 and the light regulating circuit 86. In this regard, the control of the lamp power source 81 will be described later in detail.

The light emitted from each of the light-emitting diodes 61 and 62 is first guided into each of the diverging lenses 31 and 32, respectively. In each diverging lens, the light is first converged and then diverged to illuminate an observation part (i.e., the section of the body to be observed) uniformly.

The reflected light from the observation part is guided through the imaging optical system (which includes the objective lens 33 and the convex lenses 34 and 35) to form an image on the light-receiving surface 52 of the CCD imaging sensor 5 (see FIGS. 1, 4 and 5).

Meanwhile, as shown in FIG. 2, a horizontal synchronizing signal (HS) and a vertical synchronizing signal (VS) are generated in the television timing generator 73 of the signal pre-processor 7 of the endoscope 1, and these horizontal synchronizing signal (HS) and vertical synchronizing signal (VS) are inputted into both the CCD processing circuit 72 and the CCD timing generator 74.

Further, a synchronizing signal (Sync) is generated in the television timing generator 73, and as shown in FIGS. 1 and 3, this synchronizing signal (Sync) is inputted into both the system control circuit 85 and the timing generator 95 of the signal processing circuit 9 of the light source device 8.

As shown in FIG. 2, driving signals for driving the CCD imaging sensor 5 are generated in the CCD timing generator 74 based on the horizontal synchronizing signal (HS) and the vertical synchronizing signal (VS) from the television timing generator 73, and these driving signals are outputted from the signal pre-processor 7 via the buffer 75.

Further, a sample hold signal (SHP) is generated in the CCD timing generator 74, and this sample hold signal (SHP) is inputted into the sample-hold and color-separation circuit 71.

As shown in FIG. 1, the driving signals outputted from the signal pre-processor 7 are inputted into the CCD imaging sensor 5 via the signal line 47, and the CCD imaging sensor 5 is driven based on such driving signals. Now, by driving the CCD imaging sensor 5, it becomes possible for the CCD imaging sensor 5 to take images of the observation part (namely, images formed on the light-receiving surface 52), whereupon CCD signals are outputted from the CCD imaging sensor 5. These CCD signals are inputted into the signal pre-processor 7 via the signal line 48.

As shown in FIG. 2, the sample-hold and color-separation circuit 71 of the signal pre-processor 7 separates the CCD signals into the R (red), G (green) and B (blue) color signals, respectively, in accordance with the sample hold signals (SHP) from the CCD timing generator 74. Then, the R, G and B signals are respectively inputted into the CCD processing circuit 72.

Further, in the CCD timing generator 74, clamping pulse signals (Clamp) are generated in synchronization with the timing that the R, G and B signals from the pixels of each of the shading regions 522 and 523 (shown in FIG. 5) are inputted into the CCD processing circuit 72. Then, the generated clamping pulse signals are respectively inputted into the CCD processing circuit 72.

The CCD processing circuit 72 carries out one clamping process in one horizontal scanning (i.e., per each horizontal scanning) in synchronization with the clamping pulse signals.

In each clamping process, the R, G and B signals are respectively sampled in synchronization with the respective clamping pulse signals from the CCD timing generator 74. Namely, by sampling each of the R, G and B signals from the pixels of the shading region 522 (523), a reference level of optical black can be detected, and this detected reference level can be held. (Hereinafter, the reference level of optical black is simply referred to as a "reference level.")

In the present embodiment, the CCD processing circuit 72 includes a capacitor (not shown in the drawings) which is used as a holding means for holding the reference level. Further, the capacitor is designed so as to hold the amount of charge (voltage) which corresponds to the reference level. Accordingly, the reference level can be obtained from the voltage value of such a capacitor.

Further, as shown in FIG. 2, in the CCD processing circuit 72, appropriate R, G and B signals can be obtained by subtracting the reference level component from the R, G and B signals from the pixels of the effective region 524. Based on such appropriate signals, two color-difference signals (R−Y, B−Y) and a luminance signal (Y) are generated. In this way, by subtracting the reference level component from the R, G and B signals, it becomes possible, for example, to remove useless signal components (such as the dark current component and the like) from such signals, and this makes it possible to obtain appropriate images.

As shown in FIGS. 2 and 3, the color-difference signal (R−Y), the color-difference signal (B−Y) and the luminance signal (Y) are outputted from the CCD processing circuit 72, and then inputted into the matrix circuit 91 of the signal processing circuit 9 of the light source device 8.

As shown in FIG. 1, the luminance signal (Y) is also inputted into the light regulating circuit 86, and it is used for regulating the quantity of light. Namely, a reference voltage (Vref) for regulating the light is inputted into the light regulating circuit 86 from the system control circuit 85, and based on this reference voltage (Vref) and the luminance signal (Y), the light regulating circuit 86 generates a control signal. Using the generated control signal, the light regulating circuit 86 controls the operation of the lamp power source 81. In this way, the duty cycle, that is, the ratio of the time of high-voltage level (during which the voltage level of the lamp power source 81 is high) with respect to the time of low-voltage level (during which the voltage level of the lamp power source 81 is low, that is zero volt) is adjusted, thus making it possible to properly set the quantity of light emitted from the light-emitting diodes 61 and 62.

As shown in FIG. 3, in the matrix circuit 91, the color-difference signal (R−Y), the color-difference signal (B−Y) and the luminance signal (Y) are converted into R, G and B signals, respectively.

Next, after undergoing correction by the gamma correction circuit 92 and the aperture correction circuit 93, these R, G and B signals are inputted into the A/D converter 94.

In the A/D converter 94, the R, G and B signals supplied as analog signals are converted into digital signals.

These digital R, G and B signals are temporarily written into the memory 96. In this connection, based on data corresponding to the signals stored in the memory 96, it is possible to carry out, for example, a freeze process to capture a desired still image.

Next, the R, G and B signals are read out from the memory 96 and inputted into the D/A converter 97.

In the D/A converter 97, the R, G and B signals which are supplied as digital signals are converted into analog signals. Then, the analog R, G and B signals are inputted into both the buffer 98 and the matrix encoder buffer circuit 99.

In the matrix encoder buffer circuit 99, a luminance signal (Y), a chroma signal (C) and a composite signal (Composite) are generated based on the analog R, G and B signals from the D/A converter 97 and the synchronizing signal (Sync) from the timing generator 95, and these luminance signal (Y), chroma signal (C) and composite signal (Composite) are outputted to an output terminal (not shown in the drawings).

Further, the R, G and B signals from the D/A converter 97 and the synchronizing signal (Sync) from the timing generator 95 are inputted into the television monitor 400 via the buffer 98.

Then, a color image (electronic image) taken by the CCD imaging sensor 5, namely, a color image in the form of a moving picture is displayed on the television monitor 400.

As described above, according to the endoscope 1 of the present invention, each of the light-emitting diodes 61 and 62 is provided in the tip portion 21 at a position closer to the tip end of the tip portion 21 than the CCD imaging sensor 5. Further, in the tip portion 21, each of the light-emitting diodes 61 and 62 is arranged such that a part of the light-emitting diode 61 (62) is seen so as to overlap with the shading region 522 (523) when viewed from the optical axis direction. As a result of this arrangement, it becomes possible to reduce the diameter of the main body 2, in particular, the diameter of the tip portion 21 of the main body 2.

Further, when an endoscope that is provided with such a main body having a small diameter is used as a medical endoscope, it becomes possible to relieve the pain that patients may feel during diagnosis.

Next, a second embodiment of the endoscope according to the present invention will be described.

Figure 6:
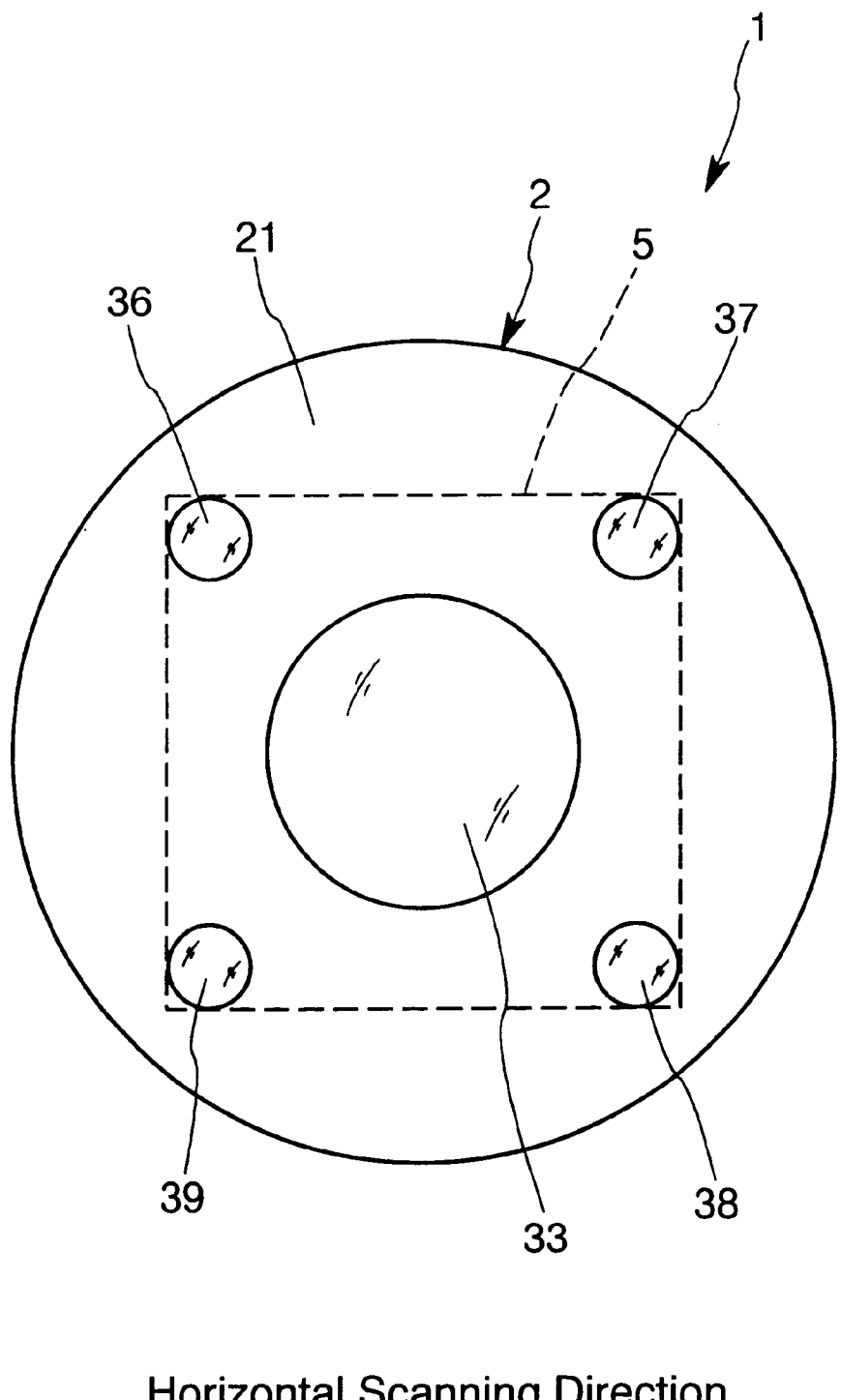
FIG. 6 is a bottom view of a tip portion of the second embodiment of the endoscope according to the present invention.
Figure 7:
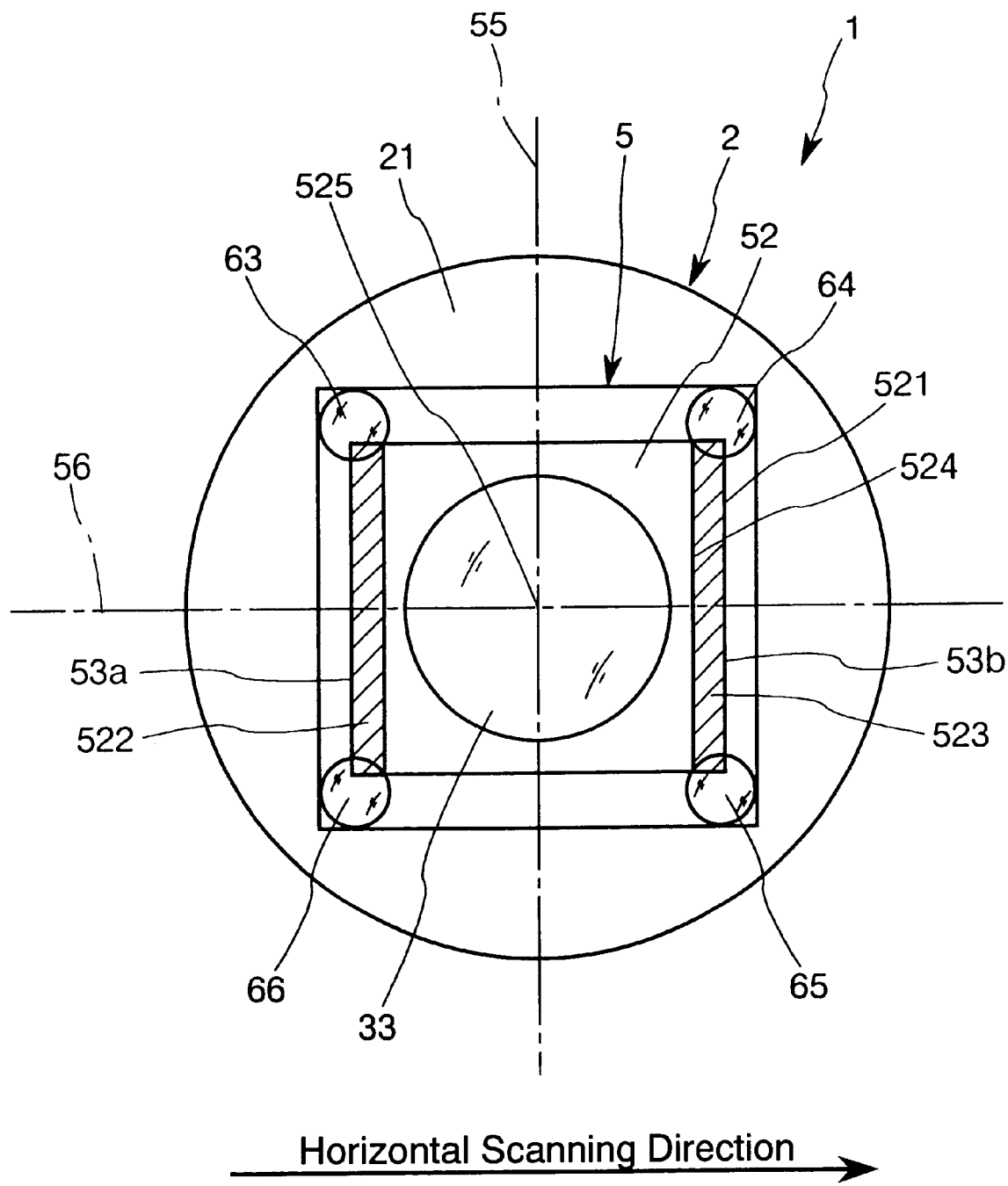
FIG. 7 is a bottom view of the tip portion of the endoscope shown in FIG. 6, in which a main body, a CCD imaging sensor, an objective lens and light-emitting diodes are shown as being viewed from the optical axis direction.

FIG. 6 is a bottom view of a tip portion of the second embodiment of the endoscope according to the present invention. FIG. 7 is a bottom view of the tip portion of the endoscope shown in FIG. 6, in which a main body, a CCD imaging sensor, an objective lens and light-emitting diodes are shown as being viewed from the optical axis direction. In this regard, a detailed description of elements and features of the second embodiment that are the same as those of the first embodiment will not be given, and only main points which are different from the first embodiment will be described.

As shown in FIGS. 6 and 7, in the tip portion 21 of the main body 2 of the endoscope 1, there are provided four diverging lenses (light distribution lenses) 36–39, and four light-emitting diodes (light-emitting elements) 63–66 which can emit white light. The diverging lenses 36–39 are respectively arranged in front of the corresponding light-emitting diodes 63–66. Namely, in the same manner as in the first embodiment, each of the diverging lenses 36–39 is arranged at the tip side of the corresponding light-emitting diode.

Each of the diverging lenses 36–39 is formed from a convex lens, and has substantially the same diameter as that of the corresponding light-emitting diode. Specifically, each of the light-emitting diodes 63–66 is arranged so that its center is substantially aligned with the center of the corresponding diverging lens when viewed from the optical axis direction.

Next, the arrangements of light-emitting diodes 63–66 in this embodiment will be described in more detail.

As shown in FIG. 7, each of the light-emitting diodes 63–66 is provided in the tip portion 21 in front of the CCD imaging sensor 5 along the optical axis O (that is, at a position closer to the tip end of the tip portion 21 than the CCD imaging sensor 5). Specifically, in the tip portion 21, each of the light-emitting diodes 63–66 is arranged such that each light-emitting diode is seen so as to be positioned on the corresponding corner section of the CCD imaging sensor 5 when viewed from the optical axis direction.

Further, in this embodiment, the light-emitting diodes 63–66 are arranged so as to satisfy the following positional relationships (i)–(iv) when viewed from the optical axis direction.

(i) The light-emitting diode 63 is seen so as to lie within the area of the CCD imaging sensor 5 with a state that a part of the light-emitting diode 63 overlaps with the shading region 522, but does not overlap with both the imaging optical system and the effective imaging region 524.

(ii) The light-emitting diode 64 is seen so as to lie within the area of the CCD imaging sensor 5 with a state that a part of the light-emitting diode 64 overlaps with the shading region 523, but does not overlap with both the imaging optical system and the effective imaging region 524.

(iii) The light-emitting diode 65 is seen so as to lie within the area of the CCD imaging sensor 5 with a state that a part of the light-emitting diode 65 overlaps with the shading region 523, but does not overlap with both the imaging optical system and the effective imaging region 524.

(iv) The light-emitting diode 66 is seen so as to lie within the area of the CCD imaging sensor 5 with a state that a part of the light-emitting diode 66 overlaps with the shading region 522, but does not overlap with both the imaging optical system and the effective imaging region 524.

Furthermore, in this embodiment, each of the light-emitting diodes 63–66 is arranged outside light rays that form an image on the effective imaging region 524 of the CCD imaging sensor 5 through the imaging optical system.

In addition, the light-emitting diodes 63–66 used in this embodiment are symmetrically positioned with respect to a first center line (straight lines) 55 that is orthogonal to the horizontal scanning direction in the CCD imaging sensor 5 and that passes through the center 525 of the effective imaging region 524 of the CCD imaging sensor 5. Further, the light-emitting diodes 63–66 are also symmetrically positioned with respect to a second center line (straight lines) 56 that is in parallel with the horizontal scanning direction in the CCD imaging sensor 5 and that passes through the center of the effective imaging region 524 of the CCD imaging sensor 5.

According to the endoscope 1 described above, it is possible to achieve the same result as those in the first embodiment of the endoscope 1.

Further, according to such an endoscope, all of the light-emitting diodes 63–66 are arranged such that each light-emitting diode is seen so as to overlap with the CCD imaging sensor 5 when viewed from the optical axis direction. By arranging the light-emitting diodes in this manner, it becomes possible to provide an endoscope with a main body which has smaller diameter than that in the first embodiment describe above.

Next, a third embodiment of the endoscope according to the present invention will be described with reference to FIGS. 8 and 9.

Figure 8:
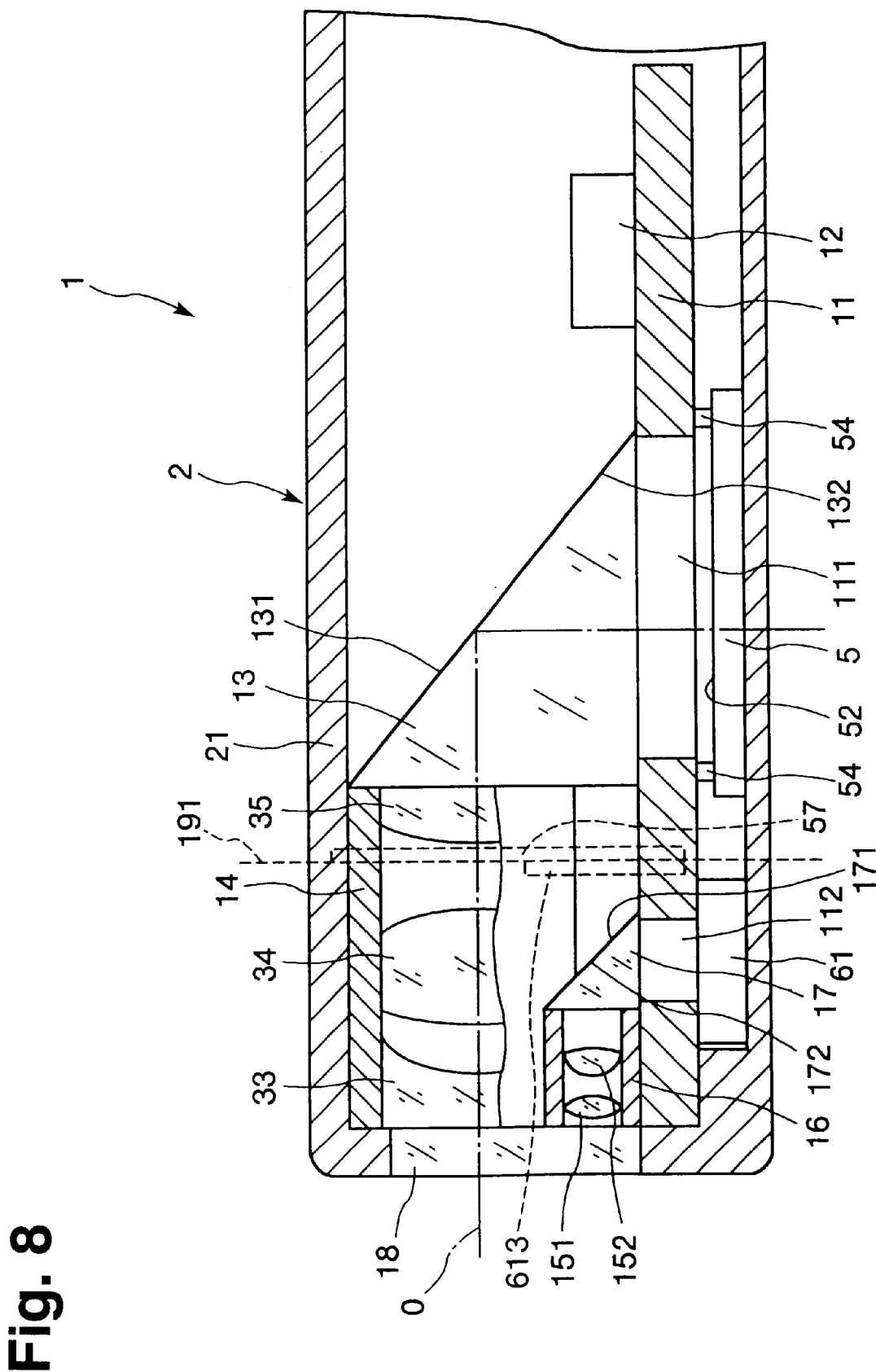
FIG. 8 is a cross-sectional view of a third embodiment of the endoscope according to the present invention, in which a tip portion of the endoscope is shown.

FIG. 8 is a cross-sectional view of the third embodiment of the endoscope according to the present invention, in which a tip portion of the endoscope is shown. FIG. 9 shows a CCD imaging sensor, a light-emitting diode, and first and second triangular prisms provided in the endoscope in FIG. 8.

Hereinafter, for easier understanding, the left side in FIGS. 8 and 9 will be referred to as "tip", and the right side will be referred to as "base". Further, an end at the side of the tip of the tip portion of the main body will be referred as a "tip end." In addition, it is to be noted that in this embodiment the optical axis is indicated by the dashed line "O" shown in FIG. 8.

In this regard, a detailed description of elements and features of the third embodiment that are the same as those of the first embodiment will not be given, and only main points which are different from the first embodiment will be described.

Figure 9:
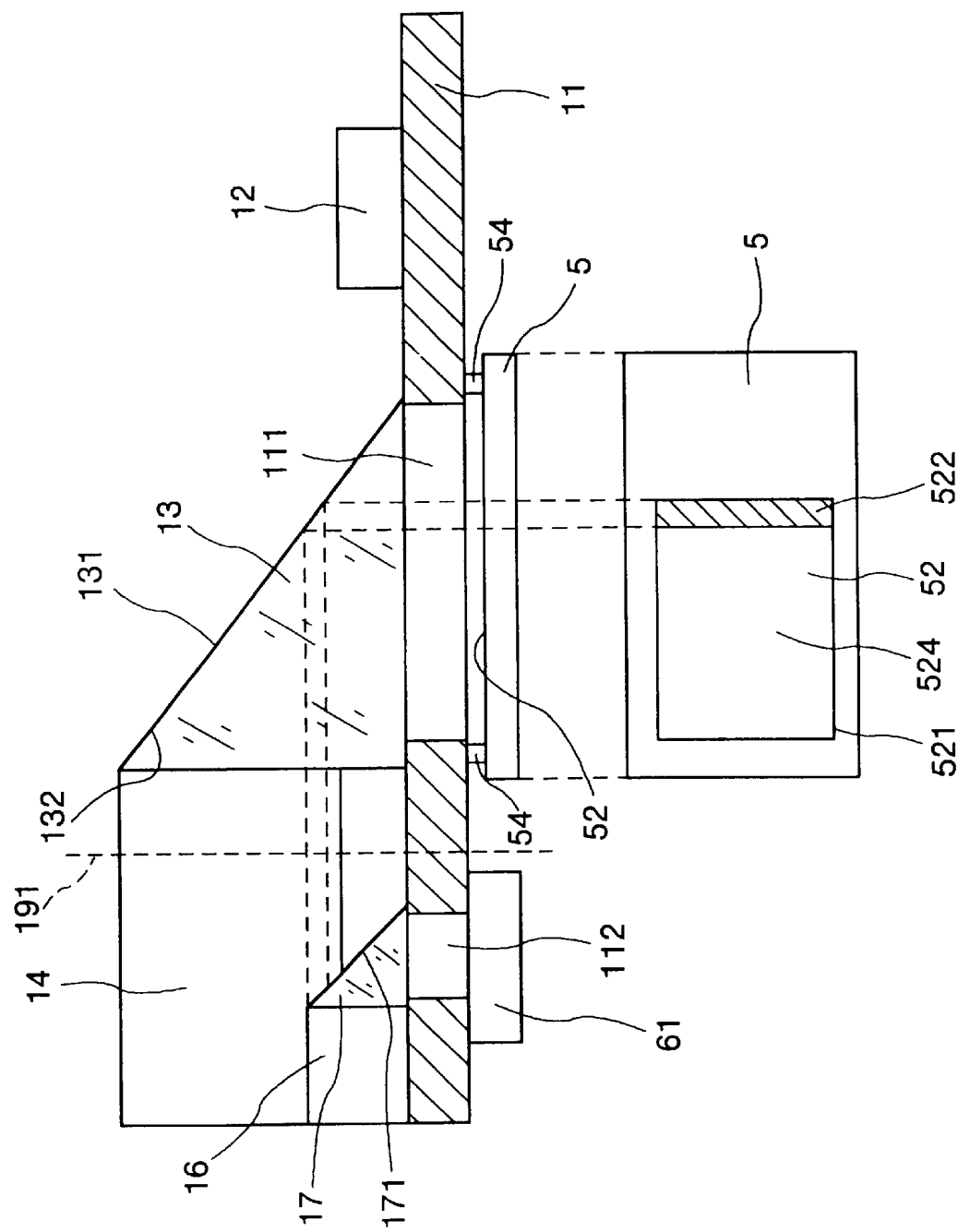
FIG. 9 shows a CCD imaging sensor, a light-emitting diode, and first and second triangular prisms provided in the endoscope in FIG. 8.

As shown in FIGS. 8 and 9, in the tip portion 21 of the main body 2, there are provided a light-emitting diode 61 and a CCD imaging sensor 5. The light-emitting diode 61 and the CCD imaging sensor 5 are arranged in a side-by-side relation ship along the longitudinal direction of the main body 2 (that is, along the left and right directions in FIG. 8). Further, the light-emitting diode 61 is arranged in the tip portion 21 at a position closer to the tip end of the tip portion 21 than the CCD imaging sensor 5.

The CCD imaging sensor 5 and the light-emitting diode 61 are mounted on a circuit board 11 provided in the tip portion 21. In addition, various devices such as an IC chip 12 shown in FIG. 8 are also mounted on the circuit board 11.

The CCD imaging sensor 5 is mounted on the circuit board 11 so that a light-receiving surface 52 thereof faces upward in FIG. 8. Further, as shown in FIGS. 8 and 9, at a position where the CCD imaging sensor 5 is mounted, an opening 111 is formed in the circuit board 11.

The light-emitting diode 61 is mounted on the circuit board 11 so that a light-emitting side thereof faces upward in FIG. 8. Further, as shown in FIGS. 8 and 9, at a position where the light-emitting diode 61 is mounted, an opening 112 is formed in the circuit board 11.

Further, in the tip portion 21 of the main body 2, a lens holder 14 is provided at a position close to the tip end of the tip portion 21 than the opening 111 of the circuit board 11. In this lens holder 14, an objective lens 33 and convex lenses 34 and 35 are mounted.

At the side of the base portion of the lens holder 14, that is, at a position of the opening 111 in the circuit board 11, there is provided a first triangular prism (light-deflecting member) 13. On the surface 131 of this first triangular prism 13, a reflection film 132 is provided. In this regard, the first triangular prism 13, the objective lens 33 and the convex lenses 34 and 35 described above constitute an imaging optical system in this embodiment.

In addition, in the tip portion 21 of the main body 2, another lens holder 16 is provided at a position closer to the tip end of the tip portion 21 than the opening 112 of the circuit board 11. In this lens holder 16, diverging lenses 151 and 152 are mounted.

At the side of the base portion of the lens holder 16, that is, at a position of the opening 112 in the circuit board 11, there is provided a second triangular prism (light-deflecting member) 17. On the surface 171 of the second triangular prism 17, a reflection film 172 is provided.

In this regard, the diverging lens 151 and 152 and the second triangular prism 17 described above constitute a lighting optical system in this embodiment.

Further, at the tip end of the tip portion 21, there is provided a transparent glass cover 18.

In this embodiment, each of the first and second triangular prisms 13 and 17 is formed from a rectangular prism.

In the endoscope 1 having the structure described above, the light-emitting diode 61 and the CCD imaging sensor 5 are arranged such that a projected image 613 (shown by a phantom line in FIGS. 8 and 9) which could be formed by projecting the light-emitting diode 61 onto a projecting surface 191 which is virtually established perpendicularly to the optical axis O overlaps with a projected image 57 which could be formed by projecting the CCD imaging sensor 5 onto the projecting surface 191.

By arranging each element in the main body 2 in this way, it becomes possible to reduce the diameter of the main body 2, in particular, the diameter of the tip portion 21 of the main body 2.

Next, arrangements of the CCD imaging sensor 5, the light-emitting diode 61 and the first and second triangular prisms 13 and 17 will be described in more detail.

As shown in FIG. 9, the light-emitting diode 61 and the second triangular prism 17 are arranged such that a part of the second triangular prism 17 is situated within the region of light rays (shown by dotted lines) being directed to the shading region 522 of the CCD imaging sensor 5. In other words, the light-emitting diode 61 and the second triangular prism 17 are arranged such that a part of a projected image which could be formed by projecting the light-emitting diode 61 (in particular, an effective region of the light-emitting diode 61) into a projecting surface 191 which is virtually established perpendicularly to the optical axis O overlaps with a projected image which could be formed by projecting the shading region 522 of the CCD imaging sensor 5 onto the projecting surface 191.

According to the arrangements described above, it is possible to dispose the CCD imaging sensor 5 at a position closer to the base end of the main body 2 as compared with the case where the second triangular prism 17 is arranged such that a part of the second triangular prism 17 is situated out of the region of the light rays being directed to the shading region 522. This arrangement allows the lens holder 14 to be provided in the tip portion 2 at a position closer to the circuit board 11. As a result, it becomes possible to reduce the diameter of the main body of the endoscope.

As shown in FIG. 8, in the endoscope 1 of this embodiment, light emitted from the light-emitting diode 61 is reflected toward the tip of the main body 2 by means of the reflection film 172 of the second triangular prism 17. Namely, when the light emitted from the light-emitting diode 61 passes through the second triangular prism 17, the light is perpendicularly deflected in the second triangular prism 17, so that the deflected light is directed toward the tip of the main body 2.

Then, the light that has passed through the second triangular prism 17 is guided into the diverging lenses 151 and 152 in the lens holder 16. In these diverging lenses, the light is first converged and then diverged to illuminate an observation part (i.e., the section of the body to be observed) uniformly.

The reflected light from the observation part passes through the imaging optical system and the first triangular prism 13. In the first triangular prism 13, the light form the imaging optical system is reflected so as to be directed toward the downside in FIG. 8. Namely, when the light form the imaging optical system passes through the first triangular prism 13, the light is perpendicularly deflected, so that the deflected light is directed toward the imaging surface 52 of the CCD imaging sensor 5 and then forms an image on the imaging surface 52.

According to the endoscope 1 described above, it is possible to achieve the same results as those in the first embodiment of the endoscope.

In this invention, no particular limitation is imposed upon the number of the light-emitting element to be provided in the endoscope. For example, two or more light-emitting elements may be provided in the endoscope of this invention.

When a plurality of light-emitting elements are provided in the endoscope 1, it is preferred that in the same manner as in the first and second embodiments the light-emitting elements are substantially symmetrically positioned with respect to the first center line 55 that is orthogonal to the horizontal scanning direction in the CCD imaging sensor 5 and that passes through the center of the effective imaging region 524 of the CCD imaging sensor 5, and with respect to the second center line 56 that is in parallel with the horizontal scanning direction in the CCD imaging sensor 5 and that passes through the center of the effective imaging region 524 of the CCD imaging sensor 5.

Next, a fourth embodiment of the endoscope of this invention will be described with reference to FIG. 10.

Figure 10:
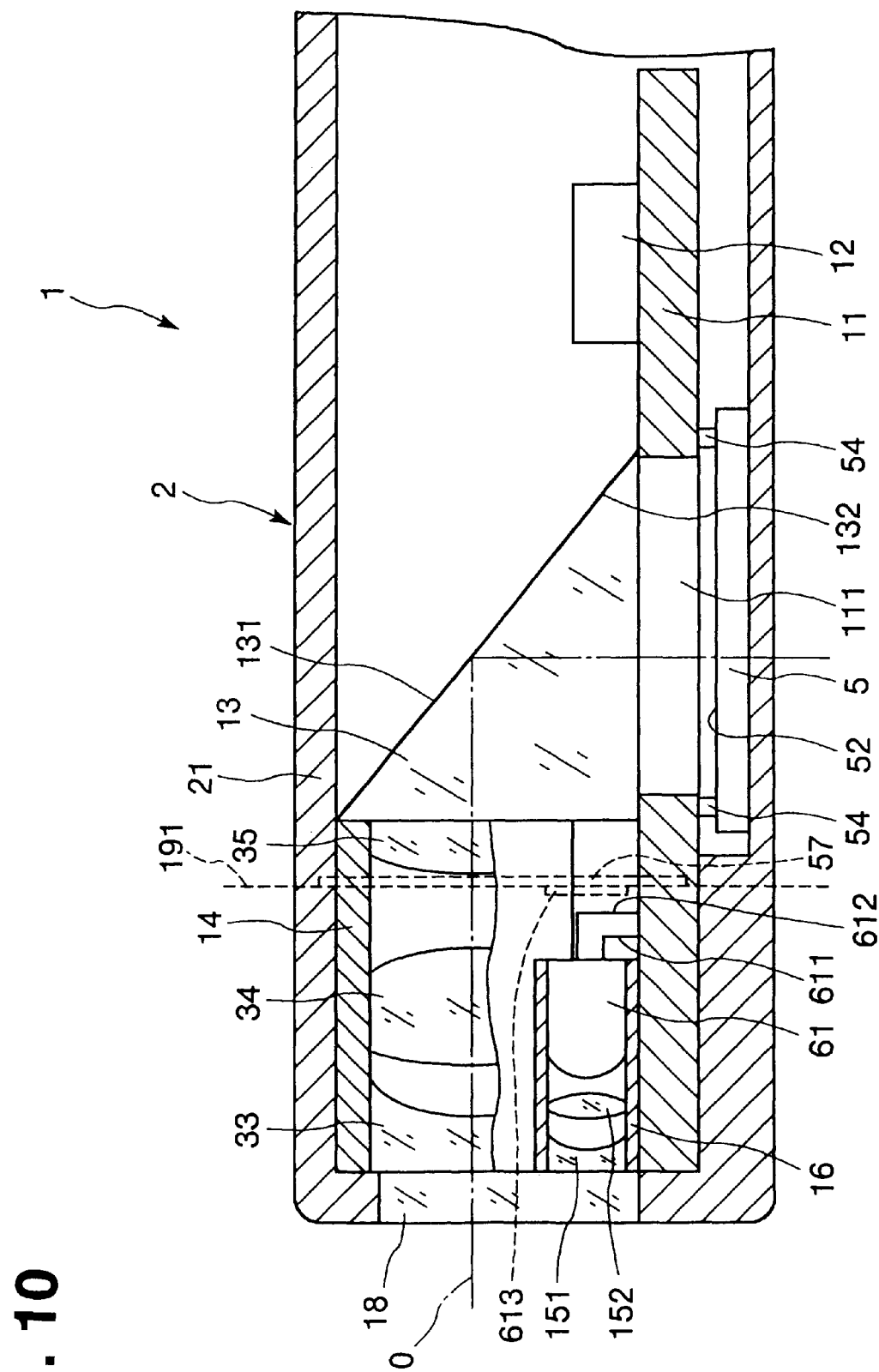
FIG. 10 is a cross-sectional view of a fourth embodiment of the endoscope according to the present invention, in which a tip portion of the endoscope is shown.
Figure 11:
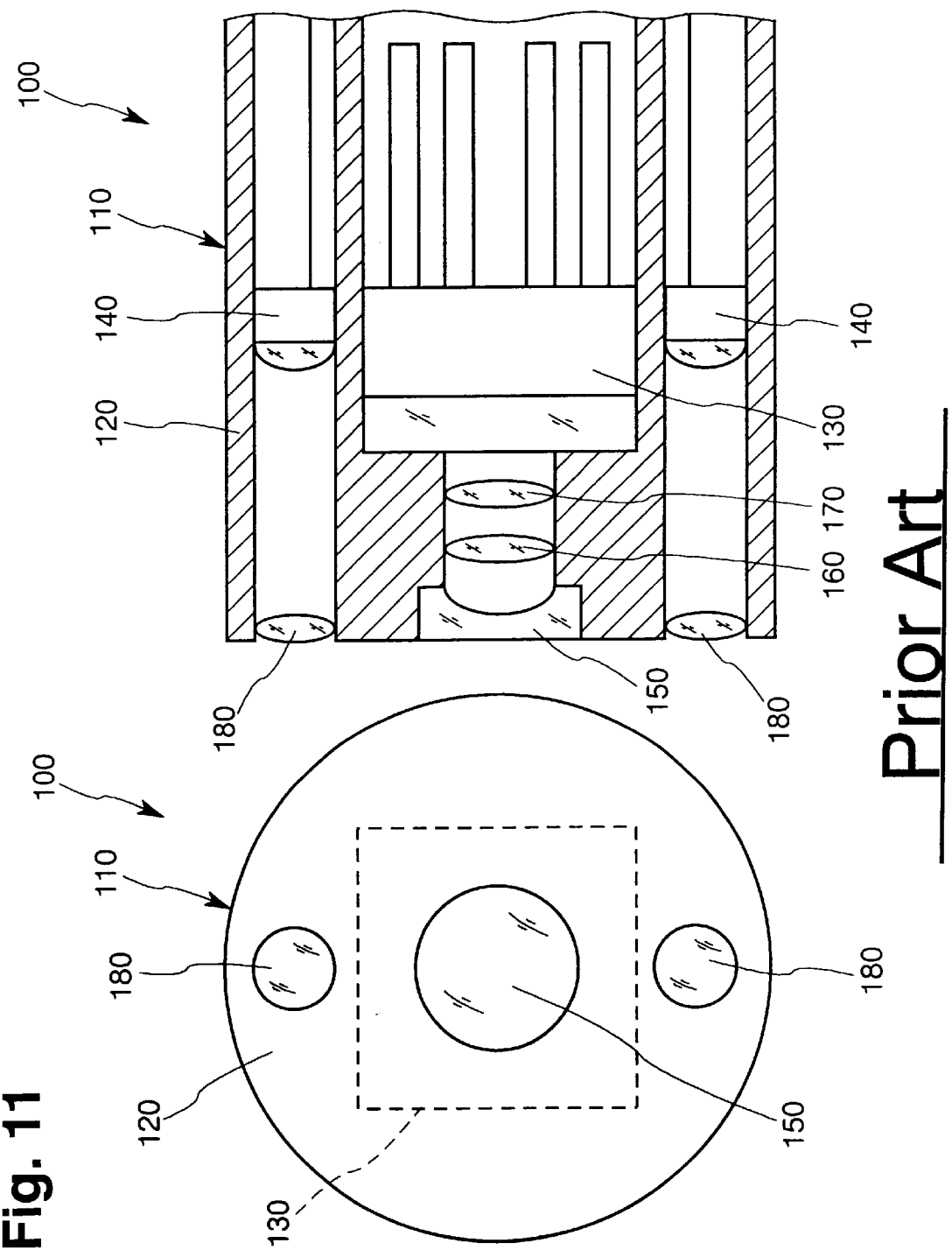
FIG. 11 is a bottom view and a cross-sectional view of a tip portion of a prior-art electronic endoscope.

FIG. 10 is a cross-sectional view of the fourth embodiment of the endoscope according to the present invention, in which a tip portion of the endoscope is shown.

Hereinafter, for easier understanding, the left side in FIG. 10 will be referred to as "tip", and the right side will be referred to as "base". Further, an end at the side of the tip of the tip portion of the main body will be referred as a "tip end." In addition, it is to be noted that in this embodiment the optical axis is indicated by the dashed line "O" shown in FIG. 10.

In this regard, a detailed description of elements and features of the fourth embodiment that are the same as those of the third embodiment described above will not be given, and only main points which are different from the third embodiment will be described.

As shown in FIG. 10, the endoscope 1 in this embodiment is provided with a light-emitting diode 61 mounted in a lens holder 16. This embodiment does not have a triangular prism like the second triangular prism 17 in the third embodiment.

The light-emitting diode 61 is electrically connected to a circuit board 11 via the lead wires 611 and 612.

In the endoscope 1 in this embodiment, the light-emitting diode 61 and the CCD imaging sensor 5 are arranged such that the light-emitting diode 61 is seen so as to overlap with the CCD imaging sensor 5 when viewed from the optical axis direction. In other words, the light-emitting diode 61 and the CCD imaging sensor 5 are arranged such that a projected image 613 which could be formed by projecting the light-emitting diode 613 onto a projecting surface 191 which is virtually established perpendicularly to the optical axis O overlaps with a projected image 57 which could be formed by projecting the CCD imaging sensor 5 onto the projecting surface 191.

Preferably, in this embodiment, as shown in FIG. 10 the light-emitting diode 61 is arranged in the main body 2 such that a part of the light-emitting diode 61 is situated within the region of light rays being directed to the shading region 522 of the CCD imaging sensor 5. Specifically, the light-emitting diode 61 is arranged in the main body 2 such that a part of a projected image which could be formed by projecting the light-emitting diode 61 onto the projecting surface 191 perpendicular to the optical axis O overlaps with a projected image which could be formed by projecting the imaging region 522 of the CCD imaging sensor 5 onto the projecting surface 191 perpendicular to the optical axis O.

According to the arrangements described above, it becomes possible to reduce the diameter of the main body 2, in particular, the diameter of the tip portion 21 of the main body 2.

Further, according to the endoscope 1 in this embodiment, it is possible to achieve the same results as in the third embodiment of the endoscope described above.

Hereinabove, the endoscope according to the present invention was described in detail, but the present invention is not limited to the embodiments described above, and it is possible to replace some of the elements with other elements so long as the same functions are achieved.

For example, in this invention, the main body 2 may be provided with one or more function channels. Examples of such a function channel include a forceps channel (lumen) through which forceps and treatment instruments such as medical laser instruments are to be passed; a water supplying channel; an air supplying channel; and the like.

Further, in the present invention, each light-emitting element is not necessarily arranged so as to overlap with the corresponding shading region when viewed from the optical axis direction. For example, in this invention, each light-emitting element may be arranged such that at least a part of the light-emitting element is seen so as to overlap with the imaging element at the side where the shading region is not placed when viewed from the optical axis direction, but not to overlap with the effective imaging region Furthermore, the endoscope of this invention may have one, three, five, or more light-emitting elements. In this regard, the number of light-emitting elements to be provided in the endoscope should be two or more, and preferably be two–eight. In these cases, the number of light-emitting elements should preferably be even number.

When the number of light-emitting elements to be provided in the endoscope is set in the manner described above, it becomes possible to produce an endoscope that can illuminate an observation part of an object more uniformly.

Further, although in the embodiments described above a light-emitting diode is used as a light emitting element, the light-emitting element to be used in the present invention is not limited to such a diode. Specifically, the endoscope or this invention may use, for example, a lamp that radiates heat and emits light when supplied electrical power thereto.

Furthermore, no particular limitation is not imposed upon imaging elements to be used in the present invention. For example, various imaging elements such as a MOS type imaging sensor, a CPD (Charge Priming Device) and the like may be used in the present invention. In this case, both a color imaging element and a monochrome imaging element can be used.

Now, it is to be noted that the endoscope of the present invention can be also applied to industrial electronic endoscopes in addition to the electronic endoscopes for medical use.

As described above, according to the present invention, it is possible to produce an electronic endoscope provided with a main body that has relatively small diameter. Further, when such an electronic endoscope is used as a medical electronic endoscope, it becomes possible to relieve the pain that patients may feel during diagnosis.

Finally, it is to be understood that many changes and additions may be made to the embodiments described above without departing from the scope and spirit of the invention as defined in the appended claims.

Further, it is also to be understood that the present disclosure relates to subject matter contained in Japanese Patent Application No. H11-344987 (filed on Dec. 3, 1999) which is expressly incorporated herein by reference in its entirety.

What is claimed is:

1. An electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion at a position closer to the tip end than the imaging element; and a light-emitting element for emitting light toward an observation part of the object, the light-emitting element being provided in the tip portion at a position closer to the tip end than the imaging element, wherein the light-emitting element is arranged such that at least a part of the light-emitting element overlaps with the imaging element when viewed from the optical axis direction of the imaging optical system, wherein the imaging element has an imaging region that includes at least one shading region for detecting a reference level of optical black, in which the light-emitting element is arranged so that at least a part of the light-emitting element overlaps with the shading region of the imaging element when viewed from the optical axis direction of the imaging optical system.

2. The electronic endoscope as claimed in claim 1, wherein the imaging optical system includes a light-deflecting member for deflecting light rays from the observation part of the object.

3. The electronic endoscope as claimed in claim 1, wherein the imaging element has an imaging region that includes an effective imaging region on which an image is to be formed by light rays that have passed through the imaging optical system.

4. The electronic endoscope as claimed in claim 1, wherein the light-emitting element includes a light-emitting diode.

5. An electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion in front of the imaging element along the optical axis;

a light-emitting element for emitting light toward an observation part of the object, the light-emitting element being provided in the tip portion at a position close to the tip end than the imaging element, wherein the light-emitting element is arranged such that at least a part of a projected image formable by projecting the light-emitting element onto a projecting surface perpendicular to the optical axis of the imaging optical system overlaps with a projected image formable by projecting the imaging element onto the projecting surface perpendicular to the optical axis; and a light-deflecting member for deflecting light rays emitted from the light-emitting element, wherein the light-deflecting member is provided in front of the light-emitting element.

6. The electronic endoscope as claimed in claim 5, wherein the imaging element has an imaging region that includes at least one shading region for detecting a reference level of optical black.

7. The electronic endoscope as claimed in claim 5, wherein the imaging optical system includes a light-deflecting member for deflecting light rays from the observation part of the object.

8. The electronic endoscope as claimed in claim 5, wherein the imaging element has an imaging region that includes an effective imaging region on which an image is to be formed by light rays that have passed through the imaging optical system.

9. The electronic endoscope as claimed in claim 5, wherein the light-emitting element includes a light-emitting diode.

10. An electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion at a position closer to the tip end than the imaging element; and a plurality of light-emitting elements for emitting light toward an observation part of the object, each of the light-emitting elements being provided in the tip portion at a position closer to the tip end than the imaging element, wherein each of the light-emitting elements is arranged such that at least a part of the light-emitting element overlaps with the imaging element when viewed from the optical axis direction of the imaging optical system, wherein the imaging element has an imaging region that includes at least one shading region for detecting a reference level of optical black, in which each of the light-emitting elements is arranged so that at least a part of the light-emitting element overlaps with the shading region of the imaging element when viewed from the optical axis direction of the imaging optical system.

11. The electronic endoscope as claimed in claim 10, wherein the imaging optical system includes a light-deflecting member for deflecting light rays from the observation part of the object.

12. The electronic endoscope as claimed in claim 10, wherein the imaging element has an imaging region that includes an effective imaging region on which an image is to be formed by light rays that have passed through the imaging optical system.

13. The electronic endoscope is claimed in claim 10, wherein the plurality of light-emitting elements include an even number of light-emitting elements, and the imaging element has an imaging region that includes an effective imaging region on which an image is to be formed, in which the light-emitting elements are substantially symmetrically positioned with respect to a center line that is orthogonal to a horizontal scanning direction in the imaging element and that passes through the center of the effective imaging region of the imaging element.

14. The electronic endoscope as claimed in claim 10, wherein each of the light-emitting elements includes a light-emitting diode.

15. An electronic endoscope having a tip portion with a tip end which is to be inserted into an object to be observed, the electronic endoscope comprising:
   an imaging element provided in the tip portion;
   an imaging optical system having an optical axis, the imaging optical system being provided in the tip portion at a position closer to the tip end than the imaging element; and
   a plurality of light-emitting elements for emitting light toward an observation part of the object, each of the light-emitting elements being provided in the tip portion at a position closer to the tip end than the imaging element, wherein each of the light-emitting elements is arranged such that at least part of the light-emitting element overlaps with the imaging element when viewed from the optical axis direction of the imaging optical system, wherein the imaging element has an imaging region that includes at least one shading region for detecting a reference level of optical black, in which each of the light-emitting elements is arranged such that at least a part of the light-emitting element is situated within the region of light rays being directed to the shading region of the imaging element.

16. The electronic endoscope as claimed in claim 15, wherein each of the light-emitting elements includes a light-emitting diode.

17. An electronic endoscope having a tip portion with a tip end which is to be inserted into an object to be observed, the electronic endoscope comprising:
   an imaging element provided in the tip portion;
   an imaging optical system having an optical axis, the imaging optical system being provided in the tip portion at a position closer to the tip end than the imaging element; and
   a plurality of light-emitting elements for emitting light toward an observation part of the object, each of the light-emitting elements being provided in the tip portion at a position closer to the tip end than the imaging element, wherein each of the light-emitting elements is arranged such that at least a part of the light-emitting element overlaps with the imaging element when viewed from the optical axis direction of the imaging optical system, wherein the plurality of light-emitting elements include an even number of light-emitting elements, and the imaging elements has an imaging region that includes an effective imaging region on which an image is to be formed, in which the light-emitting elements are substantially symmetrically positioned with respect to a first center line that is orthogonal to a horizontal scanning direction in the imaging element and that passes through the center of the effective imaging region of the imaging element, and with respect to a second center line that is in parallel with the horizontal scanning direction in the imaging element and that passes through the center of the effective imaging region of the imaging element.

18. The electronic endoscope as claimed in claim 17, wherein each of the light-emitting elements includes a light-emitting diode.

19. A electronic endoscope having a tip portion with a tip end which is to be inserted into an object to be observed, the electronic endoscope comprising:
   an imaging element provided in the tip portion;
   an imaging optical system having an optical axis, the imaging optical system being provided in the tip portion in front of the imaging element along the optical axis;
   a plurality of light-emitting elements for element light toward an observation part of the object, each of the light-emitting elements being provided in the tip portion at a position closer to the tip end than the imaging element, wherein each of the light-emitting elements is arranged such that at least a part of a projected image formable by projecting the light-emitting element onto a projecting surface perpendicular to the optical axis of the imaging optical system overlaps with a projected image formable by projecting the imaging element onto the projecting surface perpendicular to the optical axis; and
   a light-deflecting member for deflecting light rays emitted from the light-emitting element, wherein the light-deflecting member is provided in front of the light-emitting element.

20. The electronic endoscope as claimed in claim 19, wherein the imaging element has an imaging region that includes as least one shading region for detecting a reference level of optical black.

21. The electronic endoscope as claimed in claim 19, wherein the imaging optical system includes a light-deflecting member for deflecting light rays from the observation part of the object.

22. The electronic endoscope as claimed in claim 19, wherein the imaging element has an imaging region that includes an effective imaging region in which an image is to be formed by light rays that have passed through the imaging optical system.

23. The electronic endoscope as claimed in claim 19, wherein the plurality of light-emitting elements include an even number of light-emitting elements, and the imaging element has an imaging region that includes an effective imaging region on which an image is to be formed, in which the light-emitting elements are substantially symmetrically positioned with respect to a center line that is orthogonal to a horizontal scanning direction in the imaging element and that passes through the center of the effective imaging region of the imaging element.

24. The electronic endoscope as claimed in claim 19, wherein each of the light-emitting elements includes a light-emitting diode.

25. An electronic endoscope having a tip portion with a tip end which is to be inserted into an object to be observed, the electronic endoscope comprising:

an imaging element provided in the tip portion;

an imaging optical system having an optical axis, the imaging optical system being provided in the tip portion in front of the imaging element along the optical axis; and a plurality of light-emitting elements for emitting light toward an observation part of the object, each of the light-emitting elements being provided in the tip portion at a position closer to the tip end than the imaging element, wherein each of the light-emitting elements is arranged such that at least a part of a projected image formable by projecting the light-emitting element onto a projecting surface perpendicular to the optical axis of the imagine optical system overlaps with a projected image formable by projecting the imaging element onto the projecting surface perpendicular to the optical axis, wherein the plurality of light-emitting include an even number of light-emitting elements, and the imaging element of the imaging element has an imaging region that includes an effective imaging region on which an image is to be formed, in which the light-emitting elements are substantially symmetrically positioned with respect to a first center line that is orthogonal to a horizontal scanning direction in the imaging element and that passes through the center of the effective imaging region of the imaging element, and with respect to a second center line that is in parallel with the horizontal scanning direction in the imaging element and that passes through the center of the effective imaging region of the imaging element.

26. The electronic endoscope as claimed in claim 25, wherein each of the light-emitting elements include a light-emitting diode.

\* \* \* \* \*